United States Patent
Ahmed et al.

(10) Patent No.: US 11,981,641 B1
(45) Date of Patent: *May 14, 2024

(54) 4,5-BIS(4-BROMOPHENYL)-1-HEXYL-2-(3,4-DIMETHOXYPHENYL)-1H-IMIDAZOLE AS AN ANTIMICROBIAL COMPOUND

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Antar Ahmed Abdelhamid Ahmed, Sohag (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/384,698

(22) Filed: Oct. 27, 2023

(51) Int. Cl.
  *C07D 233/64*  (2006.01)
  *A61P 31/04*  (2006.01)
  *A61P 31/10*  (2006.01)

(52) U.S. Cl.
  CPC ............ *C07D 233/64* (2013.01); *A61P 31/04* (2018.01); *A61P 31/10* (2018.01)

(58) Field of Classification Search
  CPC .................................................. C07D 233/64
  See application file for complete search history.

(56) References Cited

U.S. PATENT DOCUMENTS 4,237,158 A 12/1980 Haas
2011/0152337 A1* 6/2011 Al-Qawasmeh ...... A23L 3/3544
  548/312.1

FOREIGN PATENT DOCUMENTS

EP 0584461 3/1994

OTHER PUBLICATIONS

National Center for Biotechnology Information (2023), PubChem Compound Summary for CID 122207152, 4,5-Bis(4-bromophenyl)-2-(3,4-dimethoxyphenyl)-1-[(3,4-dimethoxyphenyl)methyl]imidazole, Created Nov. 21, 2016, Retrieved Dec. 23, 2023 from https://pubchem.ncbi.nlm.nih.gov/compound/122207152 (Year: 2016).*
PubChem most relevant structure to applicants scheme 2 PA000929.
PubChem 10 most relevant structure to applicants scheme 2 PA000929.
D. S. Ambadkar et al.; "Synthesis, Charactersation and Antimicrobial Studies of Newly Synthesized 2, 4, 5-Trisubstituted-1-H-Imidazole Derivatives From 4-Methoxybenzil"; International Journal of Chemical and Physical Sciences, ISSN:2319-6602 IJCPS vol. 4 Special Issue—NCSC Jan. 2015 www.ijcps.org.
Shaaban K. Mohamed et al.; "2-(3,4-Dimethoxyphenyl)-1-pentyl-4,5-diphenyl-1H-imidazole"; Acta Crystallogr Sect E Struct Rep Online. Dec. 1, 2013; 69(Pt 12): o1833-o1834. Published online Nov. 27, 2013. doi: 10.1107/S1600536813031759.
Hashem Shargh, et al.; "One-Pot Three-Component Synthesis of 2,4,5-Triaryl-1H-imidazoles Using Mn2+ Complex of [7-Hydroxy-4-methyl-8-coumarinyl] Glycine as a Heterogeneous Catalyst"; Catalysis Letters vol. 152, pp. 1769-1783 (2022), Published: Aug. 13, 2021.
Ika Septiana et al.; "Synthesis and Docking Study of 2-Aryl-4,5-diphenyl-1H-imidazole Derivatives as Lead Compounds for Antimalarial Agent"; Indones. J. Chem., 2022, 22 (1), 105-113, Nov. 2021Indonesian Journal of Chemistry 22(1):105 DOI:10.22146/ijc.67777 License CC BY-NC-ND 4.0.
Kiran F. Shelke, et al.; "An Efficient Synthesis of 2,4,5-Triaryl-1H-Imidazole Derivatives Catalyzed by Boric Acid in Aqueous Media Under Ultrasound-Irradiation"; Bull. Korean Chem. Soc. 2009, vol. 30, No. 5; May 2009 Bulletin of the Korean Chemical Society 30(5):1057-1060 DOI:10.5012/bkcs.2009.30.5.1057.

* cited by examiner

*Primary Examiner* — Matthew P Coughlin
(74) *Attorney, Agent, or Firm* — Nath, Goldberg & Meyer; Richard C. Litman

(57) ABSTRACT

An 4,5-bis(4-bromophenyl)-1-hexyl-2-(3,4-dimethoxyphenyl)-1H-imidazole compound, its synthesis, and its use as an antimicrobial agent.

16 Claims, No Drawings

4,5-BIS(4-BROMOPHENYL)-1-HEXYL-2-(3,4-DIMETHOXYPHENYL)-1H-IMIDAZOLE AS AN ANTIMICROBIAL COMPOUND

BACKGROUND

1. Field

The present disclosure relates to an 4,5-bis(4-bromophenyl)-1-hexyl-2-(3,4-dimethoxyphenyl)-1H-imidazole compound, its synthesis, and its use as an antimicrobial agent.

2. Description of the Related Art

There remains an ongoing need for new therapeutically active agents for treating a variety of diseases, disorders, and conditions including, but not limited to, various forms of cancer, various microbial infections, and the like.

Bacterial infection remains a significant threat to human life due to its increasing resistance to conventional antibiotics, which is a growing public health concern. As a result, there is a critical need to create new antimicrobial agents with activity against potent anti-drug-resistant microorganisms.

The chemistry of heterocycles lies at the heart of drug discovery. Investigation of fortunate organic compounds for drug discovery has been a rapidly emerging theme in medicinal chemistry. Imidazoles play an important role in biological applications owing to the ring system which is present in many biological building blocks. For this reason, imidazole-derivatives have been widely utilized as anti-diabetes, anticancer, antimicrobial, anti-hypertensive anti-inflammatory, antitubercular, anti-viral, anti-oxidants, anti-coagulants, as well as depressants and lipid level modulators. Although deprotonated nitrogen atom of imidazole-derivatives can easily coordinate to various transition metal ions to form stable complex, only few studies have been reported on the antitumor activities of such type of complexes.

To achieve more environmentally friendly protocols for the synthesis of organic compounds, the redesign of reactions and modifications of existing chemical processes is often required. Among solvents, ionic liquids (ILs) have been rather sanguinely viewed as environmentally friendly or "green" solvents. Ionic liquids are non-flammable, chemically, electrochemically and thermally stable, with negligible volatility. Indeed, they are named green solvents, as their low volatility allows them to limit VOC emissions compared to conventional solvents.

Multi-component reactions (MCRs) are economically and environmentally beneficial to industry and have attracted much attention.

Thus, new molecules having desired therapeutic activities and solving the aforementioned problems are desired.

SUMMARY

The product described herein is a new imidazole derivative produced in order to provide a limited library of "drug-like" substances. 4,5-bis(4-bromophenyl)-1-hexyl-2-(3,4-dimethoxyphenyl)-1H-imidazole was synthesized via a one-pot four-component reaction of 4,4'-dibromobenzil, veratraldehyde, ammonium acetate, and hexylamine in pyridinium hydrogen sulfate as a catalyst and green solvent. The compound 4,5-bis(4-bromophenyl)-1-hexyl-2-(3,4-dimethoxyphenyl)-1H-imidazole is not only new but demonstrated excellent antimicrobial activities against different microbes. The antibacterial activity of 4,5-bis(4-bromophenyl)-1-hexyl-2-(3,4-dimethoxyphenyl)-1H-imidazole was screened against gram-positive bacteria, namely *Staphylococcus aureus*, and gram-negative bacterial strains, namely *Pseudomonas aeruginosa* and *Escherichia coli*, while the antifungal activity was screened against *Candida albicans*.

In an embodiment, the present subject matter relates to a 4,5-bis(4-bromophenyl)-1-hexyl-2-(3,4-dimethoxyphenyl)-1H-imidazole compound having the formula I:

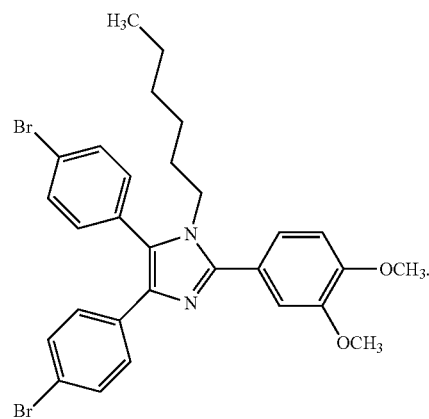

In another embodiment, the present subject matter relates to a pharmaceutically acceptable composition comprising a therapeutically effective amount of the 4,5-bis(4-bromophenyl)-1-hexyl-2-(3,4-dimethoxyphenyl)-1H-imidazole compound and a pharmaceutically acceptable carrier.

In an additional embodiment, the present subject matter relates to a method of treating a microbial infection in a patient comprising administering to a patient in need thereof a therapeutically effective amount of the 4,5-bis(4-bromophenyl)-1-hexyl-2-(3,4-dimethoxyphenyl)-1H-imidazole compound.

In one more embodiment, the present subject matter relates to a method of making the 4,5-bis(4-bromophenyl)-1-hexyl-2-(3,4-dimethoxyphenyl)-1H-imidazole compound, the method comprising: mixing 4,4'-dibromobenzil, veratraldehyde, ammonium acetate, and hexylamine in pyridinium hydrogen sulfate to obtain a solution; heating the solution in an oil bath; washing the solution and isolating yields in the solution using methyl alcohol; and obtaining the 4,5-bis(4-bromophenyl)-1-hexyl-2-(3,4-dimethoxyphenyl)-1H-imidazole compound.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a microbial infection.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The products described herein are not only new but have high antimicrobial activities. The present compound demonstrated excellent antimicrobial activities against different microbes. The antibacterial activity was screened against gram-positive bacteria, namely *Staphylococcus aureus*, and gram-negative bacterial strains, namely *Pseudomonas aeruginosa* and *Escherichia coli*, while the antifungal activity was screened against *Candida albicans*.

In an embodiment, the present subject matter relates to an 4,5-bis(4-bromophenyl)-1-hexyl-2-(3,4-dimethoxyphenyl)-1H-imidazole compound having the formula I:

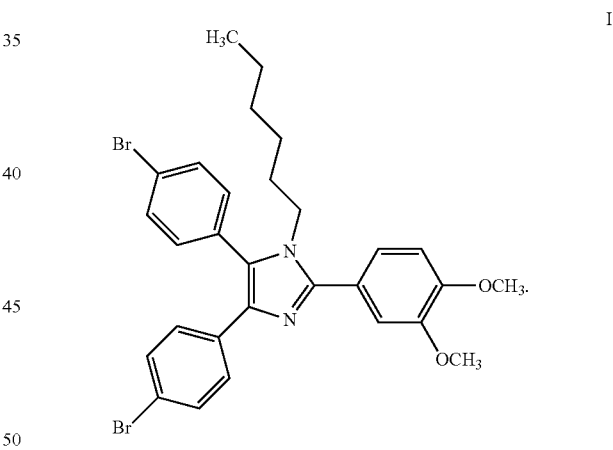

In other embodiments, the 4,5-bis(4-bromophenyl)-1-hexyl-2-(3,4-dimethoxyphenyl)-1H-imidazole compound can have a melting point of about 166° C. to about 167° C.

In another embodiment, the present subject matter relates to a pharmaceutically acceptable composition comprising a therapeutically effective amount of the 4,5-bis(4-bromophenyl)-1-hexyl-2-(3,4-dimethoxyphenyl)-1H-imidazole compound and a pharmaceutically acceptable carrier.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide treatment for a microbial infection. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treatment of a microbial infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols, or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum, and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microtine powder for insufflation, alone or in combination with an inert carrier such as lactose. In such a case, the particles of the formulation have diameters of less than 50 microns, for example less than 10 microns.

In an additional embodiment, the present subject matter relates to a method of treating a microbial infection in a patient comprising administering to a patient in need thereof a therapeutically effective amount of the 4,5-bis(4-bromophenyl)-1-hexyl-2-(3,4-dimethoxyphenyl)-1H-imidazole compound.

In certain embodiments in this regard, the microbial infection can be caused by one or more bacteria or fungi.

In an embodiment, the microbial infection can be caused by one or more gram positive bacteria. In this regard, non-limiting examples of the one or more gram positive bacterial strains causing the microbial infection include *Staphylococcus aureus*. In another embodiment, the microbial infection can be caused by one or more gram negative bacteria. In this regard, non-limiting examples of the one or more gram-negative bacterial strains causing the microbial infection include *Pseudomonas aeruginosa* and *Escherichia coli*. In a further embodiment, the microbial infection can be caused by one or more fungi. In this regard, non-limiting examples of the one or more fungi causing the microbial infection include *Candida albicans*. Any combination of any of the foregoing are further contemplated herein.

In one more embodiment, the present subject matter relates to a method of making the 4,5-bis(4-bromophenyl)-1-hexyl-2-(3,4-dimethoxyphenyl)-1H-imidazole compound, the method comprising: mixing 4,4'-dibromobenzil, veratraldehyde, ammonium acetate, and hexylamine in pyridinium hydrogen sulfate to obtain a solution; heating the solution in an oil bath; washing the solution and isolating yields in the solution using methyl alcohol; and obtaining the 4,5-bis(4-bromophenyl)-1-hexyl-2-(3,4-dimethoxyphenyl)-1H-imidazole compound.

The present production methods can be further seen by referring to the following Scheme 1:

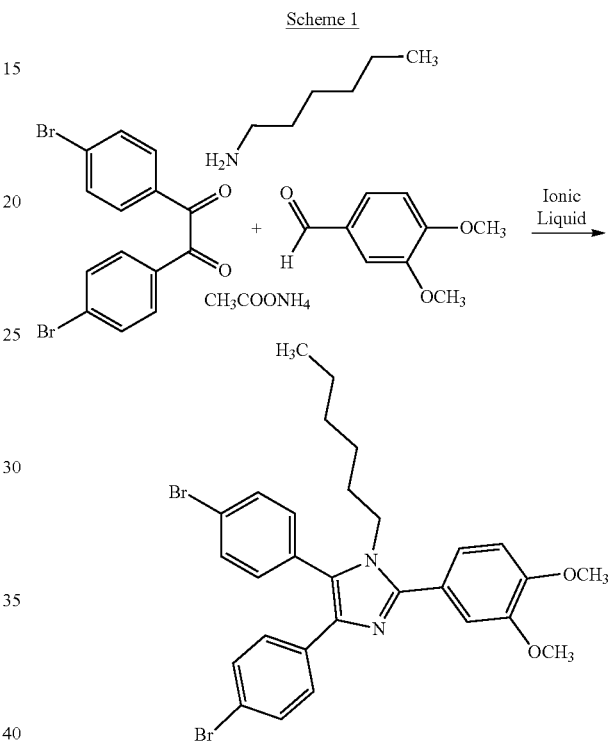

In an embodiment of the present production methods, the pyridinium hydrogen sulfate is at a temperature of about 20° C. to about 30° C., or about 25° C.

In another embodiment, the oil bath is at a temperature of about 115° C. to about 125° C., or about 120° C.

In certain embodiments of the present production methods, the solution is heated in the oil bath for at least about 5 minutes, or about 5 minutes.

In another embodiment of the present production methods, the 4,4'-dibromobenzil, the veratraldehyde, the ammonium acetate, and the hexylamine are added in about a 1:1:1:1 molar ratio.

In certain embodiments of the present production methods, the solution may be washed for at least about 3 times in water.

In certain embodiments of the present production methods, the 4,5-bis(4-bromophenyl)-1-hexyl-2-(3,4-dimethoxyphenyl)-1H-imidazole compound can be obtained in a yield of about 91%.

The following examples relate to various methods of manufacturing the specific compounds and application of the same, as described herein. All compound numbers expressed herein are with reference to the synthetic pathway figures shown above.

EXAMPLES

Example 1

Preparation of Pyridinium Ionic Liquid Catalyst Synthesis

25 mmol of Pyridine was dropped into a round bottom flask of 150 ml 3-necks with stirring. Then, 25 mmol of concentrated sulfuric acid was dropped closely to the round bottom flask in an ice bath. The combination was permitted to stir at 120° C. for 18 h (Scheme 2). After that, the yield was triple washed by diethyl ether to eliminate non-ionic molecules and dehydrated thru a rotating evaporator to yield a pure viscid liquid (pyridinium hydrogen sulfate).

Scheme 2

Example 2

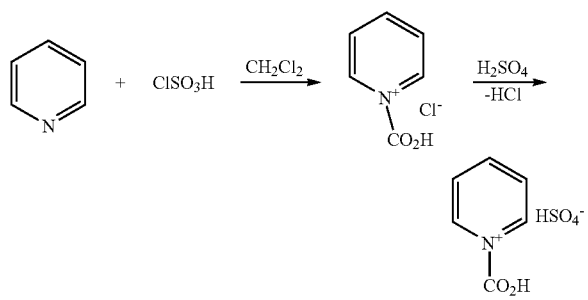

Preparation of 4,5-bis(4-bromophenyl)-1-hexyl-2-(3,4-dimethoxyphenyl)-1H-imidazole

4,4'-dibromobenzil (20 mmol), veratraldehyde (20 mmol), ammonium acetate (20 mmol), and hexylamine (20 mmol) were added to (4 mmol) pyridinium hydrogen sulfate at 25° C. (Scheme 1). The produced blend was heated in an oil bath at 120° C. for 5 minutes. To check the reaction completion thin layer chromatography method (TLC) was used. The mix was washed triple by $H_2O$ and the isolated yields were recrystallized from methyl alcohol.

Characterization Data for 4,5-bis(4-bromophenyl)-1-hexyl-2-(3,4-dimethoxyphenyl)-1H-imidazole Mp 166-167° C. yield=91%, FTIR (KBr, cm$^{-1}$): 3055 (CH arom.), 2999, 2963, 2894, 2861, 2815 (CH aliph.), 1608 (C=N), 1597 (C=C); $^1$H NMR (400 MHz, DMSO-d$_6$/D$_2$O): 0.66-0.69 (t, 3H, CH$_3$—CH$_2$—CH$_2$—CH$_2$—CH$_2$—CH$_2$—N), 0.89-0.90 (m, 4H, CH$_3$ —CH$_2$-CH$_2$—CH$_2$—CH$_2$—CH$_2$—N), 0.97-1.02 (m, 2H, CH$_3$—CH$_2$—CH$_2$-CH$_2$—CH$_2$—CH$_2$—N), 1.25-1.32 (m, 2H, CH$_3$—CH$_2$—CH$_2$-CH$_2$—CH$_2$—CH$_2$—N), 3.83 (s, 6H, 2OCH 3), 3.84-3.90 (t, 2H, CH$_3$—CH$_2$—CH$_2$—CH$_2$—CH$_2$-CH$_2$—N), 7.08-7.53 (m, 11H, CH arom.); $^{13}$C NMR (100 MHz, DMSO-d$_6$/D$_2$O): 14.03, 22.02, 25.69, 29.94, 30.60, 44.65, 56.09, 56.16, 112.28, 113.19, 121.78, 124.37, 126.41, 126.59, 128.40, 129.17, 129.50, 129.88, 131.32, 131.77, 135.34, 136.79, 147.28, 149.23, 149.89 ppm. Analysis: calculated for C$_{29}$H$_{32}$N$_2$O$_2$ (440.57): C, 79.06; H, 7.32; N, 6.36%. Found: C, 78.81; H, 7.21; N, 6.24%.

Example 3

Antimicrobial Screening

Antimicrobial Testing Methods

The antimicrobial properties of the 4,5-bis(4-bromophenyl)-1-hexyl-2-(3,4-dimethoxyphenyl)-1H-imidazole was studied by the method of agar dilution. Test solutions of each compound was prepared in concentration of 1% using dimethylformamide as a solvent then they were diluted in physiological solution to obtain the final experimental dilutions 1: 100, 1:200, 1:400, 1:800. The effect of these substances were compared with furacillin in a controlled study. The testing microbes used were gram positive bacteria *Staphylococcus aureus*, gram negative bacteria *Pseudomonas aeruginosa* and *Escherichia coli* and *Candida albicans* fungi were taken.

The experiments used for this survey were meat-pentonlu agar (EPA) for cultivation of bacteria and Saburo environment for fungi. Each experiment used 1 ml of test solution on each plate 500 min. Add 2 drops of emulsified with microbes feel. All experimental samples were taken from the agar after 10, 20, 40, 60 minutes in the environment on the basis of Patrk planted. Bacteria were cultivated at a temperature of 37° C. for 1 day and the mushroom was kept in a thermostat for 2 hours at a temperature of 28° C. Then results were checked. Those of control and the antimicrobial activity for the synthesized compounds are listed in are listed in Table 1.

TABLE 1

The antimicrobial activity of both control and 4,5-bis(4-bromophenyl)-1-hexyl-2-(3,4-dimethoxyphenyl)-1H-imidazole

| Chemical Substances | dilution rate | St. Aereus | | | | E. Coli | | | | Ps. Aeruginosa | | | | Candida albicans | | | |
|---|---|---|---|---|---|---|---|---|---|---|---|---|---|---|---|---|---|
| | | 10 | 20 | 40 | 60 | 10 | 20 | 40 | 60 | 10 | 20 | 40 | 60 | 10 | 20 | 40 | 60 |
| Furacilin | 1:100 | − | − | − | − | − | − | − | − | + | + | + | + | − | − | + | + |
| | 1:200 | + | + | + | + | + | + | + | + | + | + | + | + | + | + | + | + |
| | 1:400 | + | + | + | + | + | + | + | + | + | + | + | + | + | + | + | + |
| | 1:800 | + | + | + | + | + | + | + | + | + | + | + | + | + | + | + | + |
| 4,5-bis(4-bromophenyl)-1-hexyl-2-(3,4-dimethoxyphenyl)-1H-imidazole | 1:100 | − | − | − | − | − | − | − | − | − | − | − | − | − | − | − | + |
| | 1:200 | + | + | − | − | + | + | + | + | − | + | + | + | − | + | + | + |
| | 1:400 | + | + | + | + | + | + | + | + | + | + | + | + | + | + | + | + |
| | 1:800 | + | + | + | + | + | + | + | + | + | + | + | + | + | + | + | + |

As seen in Table 1, the antimicrobial activity 4,5-bis(4-bromophenyl)-1-hexyl-2-(3,4-dimethoxyphenyl)-1H-imidazole was analysed. 4,5-bis(4-bromophenyl)-1-hexyl-2-(3,4-dimethoxyphenyl)-1H-imidazole showed the highest inhibition activity for all tested microbes which included gram positive bacteria *Staphylococcus aureus*, gram negative bacteria *Pseudomonas aeruginosa* and *Escherichia coli* and *Candida albicans* fungi after 10, 20, 40 and 60 minutes at all dilutions 1: 100, 1:200, 1:400, 1:800.

It is to be understood that the 4-(4,5-bis(4-bromophenyl)-2-(4-methoxyphenyl)-1H-imidazol-1-yl)benzoic acid compound, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A 4,5-bis(4-bromophenyl)-1-hexyl-2-(3,4-dimethoxyphenyl)-1H-imidazole compound having the formula I:

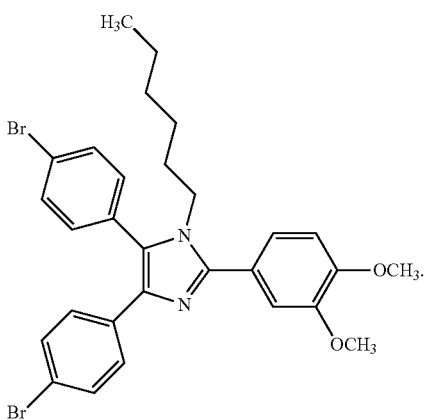

I

2. The 4,5-bis(4-bromophenyl)-1-hexyl-2-(3,4-dimethoxyphenyl)-1H-imidazole compound of claim 1, wherein the compound has a melting point of about 166° C. to about 167° C.

3. A pharmaceutically acceptable composition comprising a therapeutically effective amount of the 4,5-bis(4-bromophenyl)-1-hexyl-2-(3,4-dimethoxyphenyl)-1H-imidazole compound of claim 1 and a pharmaceutically acceptable carrier.

4. A method of treating a microbial infection in a patient comprising administering to a patient in need thereof a therapeutically effective amount of the 4,5-bis(4-bromophenyl)-1-hexyl-2-(3,4-dimethoxyphenyl)-1H-imidazole compound of claim 1.

5. The method of treating the microbial infection of claim 4, wherein the microbial infection is caused by one or more bacteria or fungi.

6. The method of treating the microbial infection of claim 5, wherein the microbial infection is caused by a gram positive bacteria, one or more gram negative bacteria, a fungus, or a combination thereof.

7. The method of treating the microbial infection of claim 6, wherein the gram positive bacteria is *Staphylococcus aureus*.

8. The method of treating the microbial infection of claim 6, wherein the one or more gram negative bacteria are *Pseudomonas aeruginosa*, *Escherichia coli*, or a combination thereof.

9. The method of treating the microbial infection of claim 6, wherein the fungus is *Candida albicans*.

10. A method of making the 4,5-bis(4-bromophenyl)-1-hexyl-2-(3,4-dimethoxyphenyl)-1H-imidazole compound of claim 1, the method comprising:
    mixing 4,4'-dibromobenzil, veratraldehyde, ammonium acetate, and hexylamine in pyridinium hydrogen sulfate to obtain a solution;
    heating the solution in an oil bath;
    washing the solution and isolating yields in the solution using methyl alcohol; and
    obtaining the 4,5-bis(4-bromophenyl)-1-hexyl-2-(3,4-dimethoxyphenyl)-1H-imidazole compound.

11. The method of making the 4,5-bis(4-bromophenyl)-1-hexyl-2-(3,4-dimethoxyphenyl)-1H-imidazole compound of claim 10, wherein the pyridinium hydrogen sulfate is at a temperature of about 25° C. during the mixing.

12. The method of making the 4,5-bis(4-bromophenyl)-1-hexyl-2-(3,4-dimethoxyphenyl)-1H-imidazole compound of claim 10, wherein the oil bath is at a temperature of about 120° C.

13. The method of making 4,5-bis(4-bromophenyl)-1-hexyl-2-(3,4-dimethoxyphenyl)-1H-imidazole compound of claim 10, wherein the solution is heated in the oil bath for about 5 minutes.

14. The method of making 4,5-bis(4-bromophenyl)-1-hexyl-2-(3,4-dimethoxyphenyl)-1H-imidazole compound of claim 10, wherein the 4,4'-dibromobenzil, the veratraldehyde, the ammonium acetate, and the hexylamine are added in about a 1:1:1:1 molar ratio.

15. The method of making the 4,5-bis(4-bromophenyl)-1-hexyl-2-(3,4-dimethoxyphenyl)-1H-imidazole compound of claim 10, wherein the solution is washed about 3 times in water.

16. The method of making the 4,5-bis(4-bromophenyl)-1-hexyl-2-(3,4-dimethoxyphenyl)-1H-imidazole compound of claim 10, wherein the 4,5-bis(4-bromophenyl)-1-hexyl-2-(3,4-dimethoxyphenyl)-1H-imidazole is obtained in a yield of about 91%.

* * * * *